United States Patent
Sumanaweera et al.

(10) Patent No.: US 6,852,081 B2
(45) Date of Patent: Feb. 8, 2005

(54) VOLUME RENDERING IN THE ACOUSTIC GRID METHODS AND SYSTEMS FOR ULTRASOUND DIAGNOSTIC IMAGING

(75) Inventors: Thilaka Sumanaweera, Los Altos, CA (US); John Cherry, San Jose, CA (US); Gianluca Paladini, Princeton, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 20 days.

(21) Appl. No.: 10/388,128

(22) Filed: Mar. 13, 2003

(65) Prior Publication Data

US 2004/0181151 A1 Sep. 16, 2004

(51) Int. Cl.$^7$ .............................................. A61B 8/00
(52) U.S. Cl. ...................................... 600/443; 128/916
(58) Field of Search .............................. 600/437–472; 128/916; 364/7, 11, 130, 138; 73/625, 626

(56) References Cited

U.S. PATENT DOCUMENTS

| | | | |
|---|---|---|---|
| 4,151,834 A | | 5/1979 | Sato et al. |
| 4,399,822 A | | 8/1983 | Theumer |
| 5,483,963 A | * | 1/1996 | Butler et al. ................ 600/437 |
| 5,515,856 A | * | 5/1996 | Olstad et al. ............... 600/440 |
| 5,678,554 A | | 10/1997 | Hossack et al. |
| 6,043,589 A | | 3/2000 | Hanafy |
| 6,057,632 A | | 5/2000 | Ustuner |
| 6,312,381 B1 | * | 11/2001 | Knell et al. ................. 600/437 |

OTHER PUBLICATIONS

"IVoR: Interactive and Intuitive Volume Rendering of 3D–Medical Data With 3D–Texture Mapping Technique," by Huseyln Kemal Cakmak; F.A. University Eriangen/Nbg. Mar. 15, 1996–Sep. 16, 1996.

"Real Time 3D Visualization of Ultrasonic Data Using Standard PC," by Svetoslav Ivanov Nikolov, Juan Pablo Gomez Gonzalez, Jorgen Arendt Jensen, Jun. 12, 2001.

"Real Time 3D Visualsation of Ultrasonic Data Standard PC," by Svetoslav I. Nikolov, Juan P.G. Gonzalez, and Jorgen A. Jensen; Jun. 12, 2001.

"Real Time Ultrasound Scan Conversion Algorithm On Programmable Mediaprocessors," by Chris Basoglu, Yongmin Kim, and George York; Abbreviated Journal Title—Proc SPIE Int Soc Opt Eng vol. 3335, p. 252–262, 1998.

"Real Time Algorithm For Generating Color Doppler Ultrasound Images on Commercially Available Microprocessors," by Chris Basoglu and Yongmin Kim; Proceedings of SPIE—The International Society of Optical Enginering; vol. 3031, 1997: Society of Photo–Optical Instrumentation Engineers, Bellingham, WA, USA: p. 385–396, 1997.

"Interactive Three–Dimensional Ultrasound Using a Programmable Multimedia Process," by W.S. Edwards, C. Deforge, and Y. Kim; Abbreviated Journal Title—Int. J. Imaging System Technol. (USA) vol. 9, No. 6, p. 442–54, 1998.

"Programmable Ultrasound Imaging Using Multimedia Technologies: A Next–Generation Ultrasound Machine," by Y. Kim, J.H. Kim, C. Basoglu, and T.C. Winter; IEEE Trans Inf technol Biomed; p. 19–29; Mar. 1997.

\* cited by examiner

*Primary Examiner*—Ali Imam

(57) ABSTRACT

Methods and systems for volume rendering three-dimensional ultrasound data sets in an acoustic grid using a graphics processing unit are provided. For example, commercially available graphic accelerators cards using 3D texturing may provide 256x, 256×128 8 bit volumes at 25 volumes per second or better for generating a display of 512×512 pixels using ultrasound data. By rendering from data at least in part in an acoustic grid, the amount of scan conversion processing is reduced or eliminated prior to the rendering.

19 Claims, 12 Drawing Sheets

VOLUME RENDERING IN THE ACOUSTIC GRID METHODS AND SYSTEMS FOR ULTRASOUND DIAGNOSTIC IMAGING

BACKGROUND

The present invention relates to three-dimensional imaging. In particular, three-dimensional (3D) imaging uses data acquired in a different format than the display format.

Volume rendering generates two-dimensional images from three-dimensional data volumes. MRI, CT and ultrasound use volume rendering for three-dimensional imaging. Typically, software that is computationally expensive and time consuming implements volume rendering.

Ultrasound data formatted in a display Cartesian coordinate grid are volume rendered using graphic accelerators, such as graphic accelerators for general purpose personal computers. The data is interpolated or scan converted along a Cartesian coordinate 3D grid before volume rendering. Three-dimensional texturing using application programming interfaces, such as OpenGL or DirectX, is used to render the three-dimensional data set.

BRIEF SUMMARY

The present invention is defined by the following claims, and nothing in this section should be taken as a limitation on those claims. By way of introduction, the preferred embodiments described below include methods and systems for volume rendering three-dimensional data sets in an acoustic or other non-Cartesian grid in real time using graphics accelerators. For example, commercially available graphic accelerators cards using 3D texturing may provide 256×, 256×128 8 bit volumes at 25 volumes per second or better for generating a display of 512×512 pixels using ultrasound data. By rendering from data at least in part in an acoustic grid, the amount of scan conversion processing is reduced or eliminated prior to the rendering.

In a first aspect, a method for volume rendering ultrasound data for three-dimensional imaging is provided. Ultrasound data formatted at least in part in an acoustic grid is loaded into a graphics processing unit. The graphics processing unit volume renders from the ultrasound data.

In a second aspect, an ultrasound system for volume rendering ultrasound data for three-dimensional imaging is provided. A memory is operable to store ultrasound data formatted at least in part in an acoustic grid. A graphics processing unit connects with the memory. The graphics processing unit is operable to volume render from the ultrasound data formatted at least in part in an acoustic grid.

Further aspects and advantages of the invention are described below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS 3D texture processing in the graphics processing unit (GPU) provides volume rendering from data in an acoustic or non-Cartesian coordinate grid. In one embodiment, real time rendering, such as 25 volumes a second or better, is provided using a commercially available personal computer graphics accelerator card. The volume rendering maps the data in the acoustic grid as a two-dimensional image, giving the perception of seeing a variable density cloud with depth cues, and 3D textures implemented with OpenGL DirectX or another application programming interface (API) provides for rapid volume rendering.

I. Ultrasound System for Volume Rendering

Figure 1:
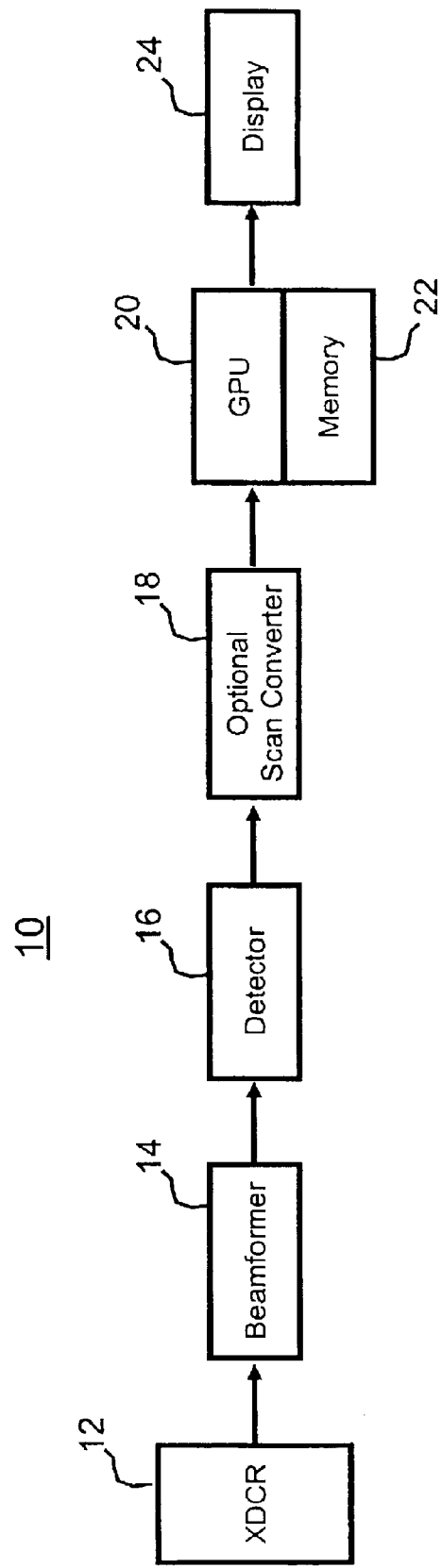
FIG. 1 is a block diagram of one embodiment of an ultrasound system for volume rendering ultrasound data.

FIG. 1 shows an ultrasound system 10 for volume rendering ultrasound data for 3D imaging. The ultrasound system 10 includes a transducer 12, a beamformer 14, a detector 16, an optional scan converter 18, a GPU 20 with a memory 22, and a display 24. Additional, different or fewer components may be provided, such as providing a control processor for configuring the system 10 and providing scan position information to or from the beamformer 14 to the GPU 20 or memory 22 and/or providing another processor for generating triangles or quadrilaterals used in texture mapping by the GPU 20.

The transducer 12 comprises a 1, 1.25, 1.5, 1.75, or two-dimensional array of elements. The array of elements is configured as linear, curvilinear, sector, Vector®, or other imaging configurations. In one embodiment, the transducer 12 is configured to allow electrical steering on the transmitand receive-beams in two dimensions, such as steering along an azimuthal axis and an elevation axis. For example, one or two rows of elements are configured for steering in the azimuthal direction electronically in response to delays and apodization and in the elevation direction in response to frequency, such as disclosed in U.S. Pat. No. 6,043,589; 5,678,554; and 6,057,632, the disclosures of which are incorporated herein by reference. Variations in the thickness of the transducer along the range dimension as a function of elevation allow for frequency based steering in elevation. As another example, a one-dimensional or multi-dimensional array is mechanically wobbled or steered in the elevation dimension, such as disclosed in U.S. Pat. Nos. 4,151,834 and 4,399,822, the disclosures of which are incorporated herein by reference. In other embodiments, the transducer 12 comprises a multi-dimensional array for steering in the elevation and azimuthal dimensions in response to relative delays and apodization. Alternatively, the transducer 12 comprises a linear array or multi-dimensional array for electronically steering in the azimuthal dimension and for orienting in the elevation dimension in response to user movement of the transducer 12. As yet another alternative, a transducer that is rotatable around a range axis allows scanning a volume. Other transducers now known or later developed for steering in an elevation and azimuthal dimensions may be used.

The beamformer 14 comprises a transmit and/or receive beamformer, such as waveform generators, waveform memories, delays, amplifiers, counters, transistors, switches, filters, summers, or other devices for transmitting and receiving along scan lines. The beamformer 14 controls delays, apodization, frequency or other electrical characteristic and/or controls a mechanical positioning or sensing of the position of the transducer 12 for electrically and/or mechanically focusing the array of elements of the transducer 12 along one or more scan lines. The beamformer 14 connects with the transducer 12 for generating acoustic beams along an acoustic grid corresponding to the scan lines. For example, a polar coordinate format is used in a two-dimensional plane or a three-dimensional volume to acquire signals representing range samples along scan lines within the plane or volume. The acoustic data is collected by rocking, rotating, or sliding the transducers with mechanical movement or using electronic beam steering. In a polar coordinate format acoustic grid, the scan lines are at a same or different angles in one or both of the azimuth and elevation dimensions, emanate from a same or different points along the face of the transducer dimensions) and are sampled along a range dimension. In alternative embodiments, a cylindrical grid or other coordinate system is used. The scan lines are parallel, such as associated with linear imaging or diverging, such as associated with sector or Vector® scanning. The acoustic grid comprises a sample pattern defined by the various scan lines and sampling along the scan lines. The sampling of acoustic information is in a Cartesian grid, polar grid, hexagon grid, cylindrical grid or other grid system. Where the sampling is along a Cartesian grid, such as using a linear array, the sampling is likely on a larger scale or with a different resolution than the display Cartesian grid. As a result, scan conversion is typically performed on such data, but may be minimized or eliminated using the processes described herein.

The detector 16 comprises a B-mode, Doppler, flow or other detector for identifying intensity, energy, velocity or other information from the beamformer signals.

The optional scan converter 18 comprises a processor, application specific integrated circuit, digital circuitry, multiplexer, latches, shifters, digital circuitry, analog circuitry or combinations thereof for converting from the acoustic grid to a Cartesian coordinate grid, such as associated with a display. Where the three-dimensional representation is rendered from data free of formatting along a Cartesian coordinate, the scan converter 18 is skipped, not provided, or turned off. In embodiments where some data is formatted in a Cartesian coordinate system, the scan converter 18 converts some data from the acoustic grid to the Cartesian coordinate grid. For example, the scan-converter 18 scan-converts a plurality of two-dimensional images or planes from an acoustic grid to a Cartesian coordinate grid. Where each of the planes represents a different plane within the scanned volume, the planes are positioned relative to each other as part of the acoustic grid without scan-conversion into an entirely 3D Cartesian grid. Each plane comprises ultrasound in a display Cartesian coordinate grid.

The memory 22 comprises a video random access memory, a random access memory, a removable media (e.g. diskette or compact disc) or other memory device for storing data or video information. In one embodiment, the memory 22 comprises a video random access memory of a graphics processing unit or accelerator card. In alternative embodiments, the memory 22 is separate from the graphics processing unit 20, such as a cache memory of a processor, the system memory or other memory. The memory 22 is operable to store ultrasound data formatted in an acoustic grid or at least in part an acoustic grid, such as data in both a Cartesian coordinate grid and acoustic grid.

The GPU 20 comprises a graphics accelerator chip, processor, applications specific integrated circuit, circuit, or cord. In one embodiment, the GPU 20 comprises a personal computer graphics accelerator card or components, such as manufactured by nVidia (e.g. Quadro4 900XGL or others), ATI (e.g., Radion 9700 or others), or Matrox (Perihelia or others). The GPU 20 provides hardware devices for accelerating the volume rendering processes, such as using application programming interfaces for three-dimensional texture mapping. Example APIs include OpenGL and DirectX, but other APIs may be used independent of or with the GPU 20. The GPU 20 is operable to volume render the ultrasound data, such as volume rendering from ultrasound data free of conversion to a Cartesian coordinate format or ultrasound data including data both in a Cartesian coordinate format and acoustic format. The GPU 20 is operable to texture map with alpha blending or other volume rendering of the ultrasound data based on a spatial relationship of an intersection of a plane or a curved surface perpendicular to the viewing direction with an acoustic grid or data space.

The GPU 20 and/or the memory 22 are included within the system as part of a single ultrasound system component, such as an ultrasound system on a cart in a same housing. In alternative embodiments, the GPU 20 and memory 22 are provided separate from an ultrasound data acquisition system, such as provided in a workstation or personal computer. The ultrasound data at least in part in the acoustic grid is transferred wirelessly, over a computer network or through a transferable storage medium to the GPU 20.

The display 24 comprises a CRT, LCD, flat panel, plasma screen, video projector or other device for displaying a two-dimensional representation of a three-dimensional volume. For example, the display 24 comprises a color display capable of 512×512 of pixels area, but greater or lesser resolutions may be provided. Monochrome displays are used in alternative embodiments.

Using a user interface of the system 10 in conjunction with the GPU 20 and the display 24, the user views renderings of the ultrasound data from various viewing angles to perceive a three-dimensional view from the two-dimensional display. Each representation is associated with a different viewing angle. Using a same set of acoustic data or a continuing stream of acoustic data, multiple two-dimensional representations of the three-dimensional volume are provided. In one embodiment, the GPU 20 is operable to generate images of at least 512×512 pixels at 25 times or more a second for real time imaging. By continuous scanning by the beamformer 14 or continuous input of data, the GPU 20 generates two-dimensional representations from any of various angles of a scanned volume showing changes within the scanned volume seemingly as they occur. Frame rates of 25 frames or more a second are generally associated with real-time scanning. By using the hardware acceleration of the GPU 20 and minimizing or eliminating the scan-conversion step, more rapid volume rendering is provided for real time imaging. In one embodiment, a volume associated with 256×256×128 samples of 8 bit data are provided at 25 volumes per second rendering 512×512 pixels images also at about 25 images a second. Preferably, the two-dimensional representations have minimal artifacts, such as little or barely noticeable Moiré patterns or stair stepping patterns from under-sampling.

II. Wire Frame Model

Different wire frame models may be used, such as data formatted entirely in an acoustic grid and data formatted in part in an acoustic grid. The three-dimensional ultrasound data loaded into the memory 22 is a string of data samples. The three-dimensional ultrasound data are arranged as a collection of L two-dimensional data arrays, each two-dimensional data array L containing M one-dimensional data arrays and each one-dimensional data array M containing N ultrasound data samples. The two-dimensional data arrays L are spatially different from one another, including differences associated with translation and/or rotation with respect to one or more axes. In one example, a one-dimensional transducer 12 is translated along its elevation direction and/or rocked around its azimuthal direction while acquiring a series of parallel or near-parallel two-dimensional images. In another example, the one-dimensional transducer 12 is rotated around its range direction while acquiring a series of two-dimensional images. A two-dimensional transducer 12 can also be used to acquire the two-dimensional images. The two-dimensional images may or may not be scan-converted in two-dimensions. The data in each of the two-dimensional data arrays L may be associated with a plane in the patient, but alternatively may not have come from physical points that are in a plane. In the more general case, the data samples in the one-dimensional data arrays M are within a same plane, but alternatively may not have come from points that are coplanar in the physical object that is being scanned. For example, each of the two-dimensional data arrays L may contain data samples coming from points that are on a planar surface or a curved surface.

Figure 3:
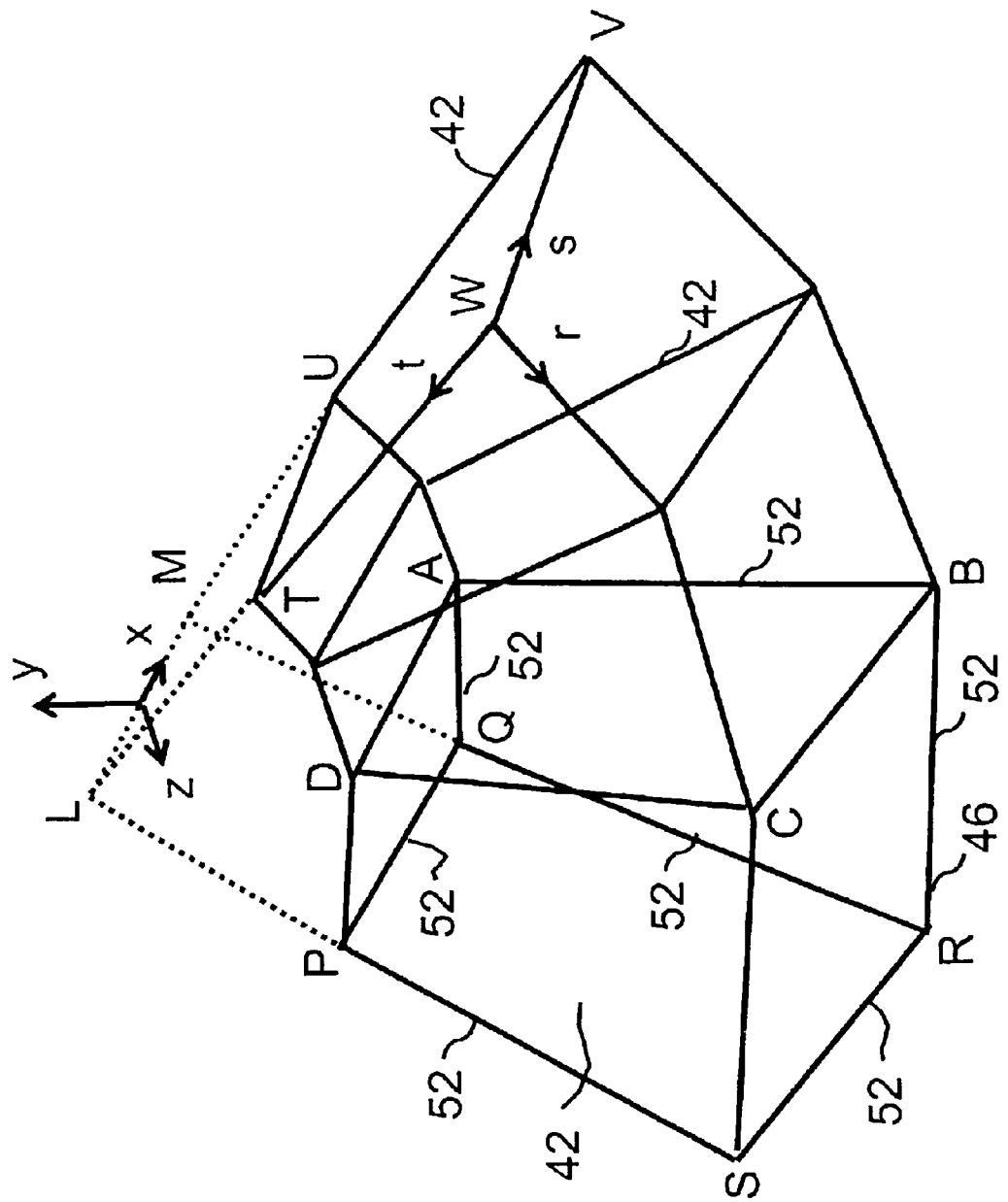
FIG. 3 is a graphical representation of a first embodiment of a wire frame model for the case where the three-dimensional ultrasound data set contains partially scan-converted data.
Figure 9:
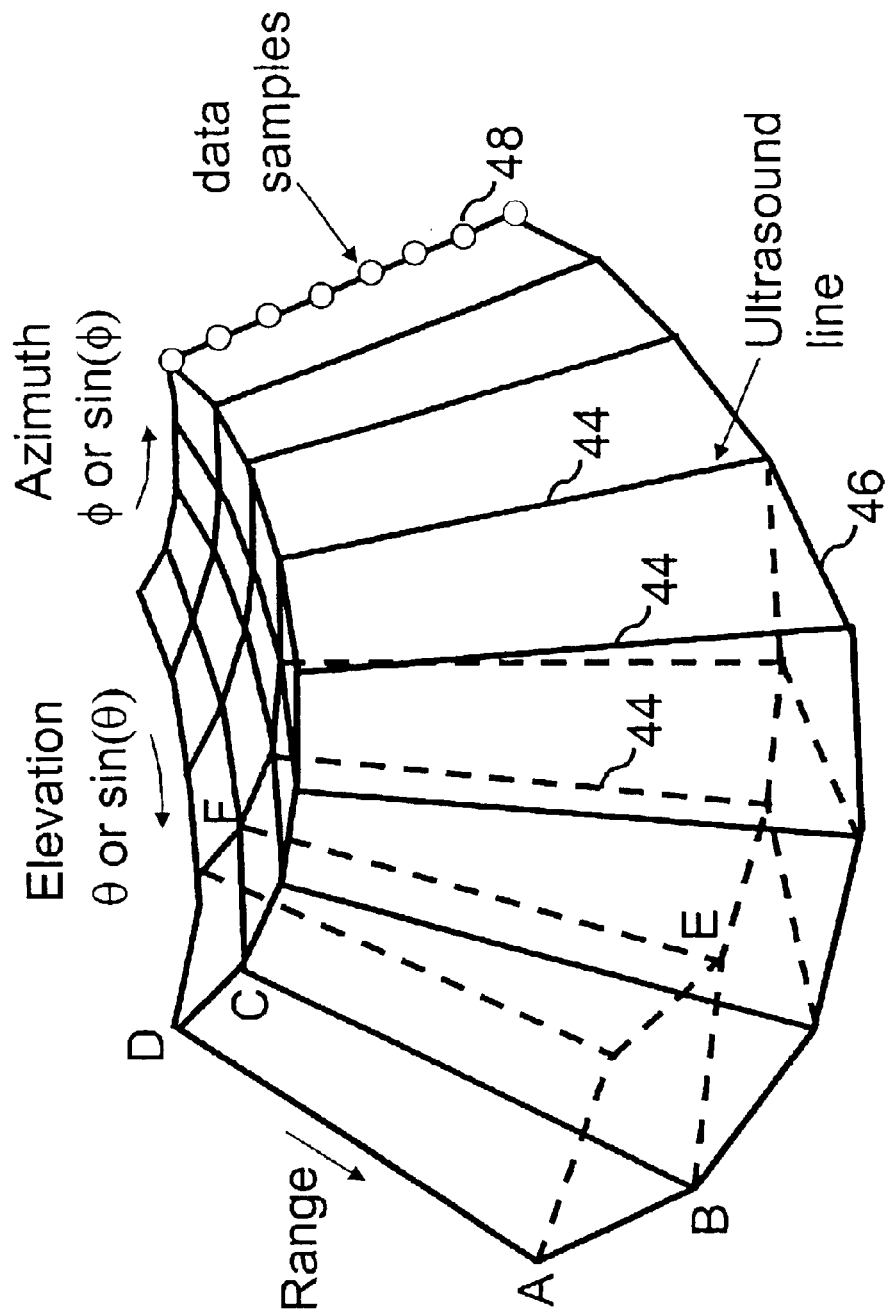
FIG. 9 is a graphical representation of a second embodiment of a wire frame model for the case where the three-dimensional ultrasound data set contains no scan-converted data.
Figure 10:
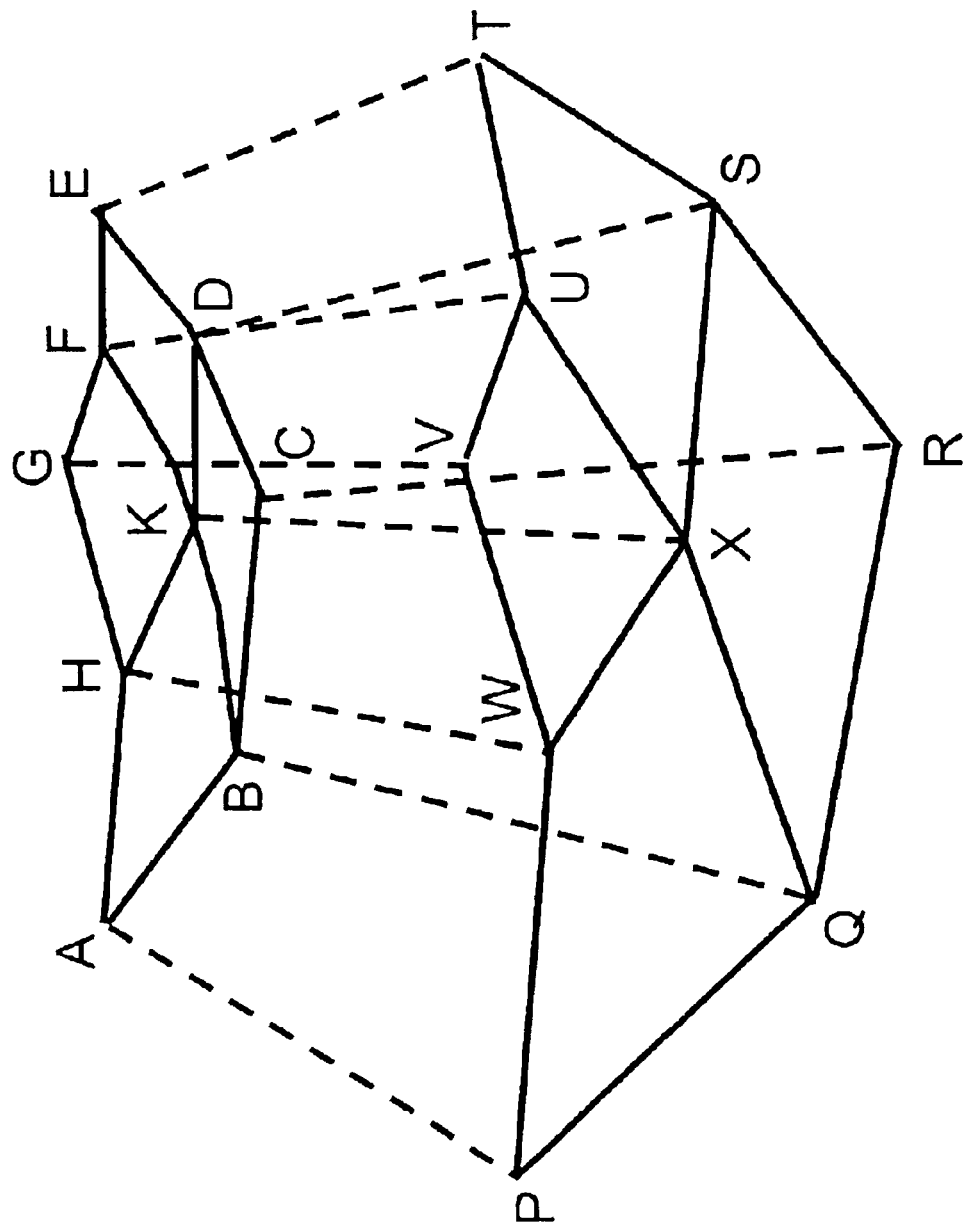
FIG. 10 is a graphical representation of a simplified second embodiment of the wire frame model of FIG. 9 showing only nine ultrasound lines.

The geometry of the three-dimensional ultrasound data is defined using a wire frame model associated with the data set. FIG. 3 shows a first embodiment of the wire frame model 46 while FIGS. 9 and 10 show a second embodiment of the wire frame model 46. The wire frame models 46 are a collection of three-dimensional points, lines and surfaces. The points of the wire frame model are referred to herein as nodes, the lines as edges 52 and surfaces as sides 42. The wire frame model 46 is a collection of nodes, edges 52 and sides 42 in three-dimensional space, along with spatial relationships amongst the nodes, edges 52 and sides 42. The nodes are expressed using three Cartesian coordinates, such as x, y and z. Each edge 52 links a pair of nodes. Each node is attached to several edges 52. Each side 42 is bounded by a set of edges 52, typically but not necessarily, four, and a set of nodes, also typically but not necessarily, four.

In FIG. 3, the wire frame model 46 corresponds to a three-dimensional ultrasonic data set of a plurality of scan-converted planes of data, spaced along the elevation direction. Each plane of data corresponds to a side 42. For example, a series of two-dimensional images are acquired by moving a one-dimensional transducer along its elevation direction or by firing a series of non-coplanar two-dimensional images by a two-dimensional transducer. Each of the two-dimensional images comprises data that is scan-converted in two-dimensions. Alternatively, in each two-dimensional image, such as DABC, the ultrasound lines are parallel to each other and no scan-conversion has been performed. For example, the three-dimensional ultrasound data is generated by moving a one-dimensional linear transducer along its elevation direction or by firing a series of parallel ultrasound lines in each of the non-coplanar two-dimensional images by a two-dimensional transducer. Scan-conversion has not taken place along a direction that is substantially along the elevation direction of any given image.

In FIG. 3 only four scan-converted sides 42 are shown for clarity. In practice, the wire frame model may contain many more scan-converted sides 42. For example, rectangle PQRS is a two-dimensional scan-converted image plane. The next two-dimensional scan-converted image plane is ABCD, and so on. The rectangle PQRS may or may not be parallel to the rectangle ABCD. The nodes of the wire frame model 46 are the corners such as P, Q, R, S, A, B, C, D . . . of the two-dimensional images of data 42. The edges 52 of the wire frame model are formed partially from the edges of the two-dimensional images. The wire frame model 46 also contains edges 52 formed by linking corresponding nodes of successive two-dimensional images. For example, the corner Q and the corner A of two different images are linked using edges 52. The sides of the wire frame model 46 are the first two-dimensional ultrasound frame, PQRS, the last two-dimensional ultrasound frame, the sides 42 at the bottom of the wire frame model 46, such as BCSR and the sides 42 at the top of the wire frame model such as PDAQ in FIG. 3. Note that the "internal sides," such as ABCD, corresponding to the two-dimensional ultrasound data frames that are neither the first nor the last frames are excluded from the sides of the wire frame model in one embodiment. In other words, there are no sides 42 that are "internal" to the wire frame model 46. In alternative embodiments, sides 42 are provided within the wire frame model 46.

In the preceding description, if there are L two-dimensional images in the three-dimensional volume, there are L sides 42, such as PQRS, ABCD . . . each corresponding to one two-dimensional image. In practice, the number of planes such as PQRS, ABCD . . . in the wire frame model can be reduced for a given L, say to L/2, resulting in increased processing speed, at the expense of image quality of the final volume rendered image.

The Cartesian coordinate system of the wire frame model 46, (x, y, z), is also shown in FIG. 3. The coordinates of the nodes of the wire frame model 46 are defined in the Cartesian coordinate system, (x, y, z). The two-dimensional ultrasound data frames are assumed to intersect at the line LM, but other configurations with one, more or all planes not intersecting a common line may be used. The origin of the Cartesian coordinate system is located at the mid-point of line LM, but may be located elsewhere. The x-axis is along line LM, the y-axis is normal to LM and pointing up and the z-axis is normal to both x- and y-axes. Other definitions of the Cartesian system may also be used.

FIG. 9 shows the second embodiment where the wire frame model 46 of a plurality of ultrasound lines 44 is shown. In this case, the ultrasound data is free of scan-conversion. For example, the ultrasound data is acquired by collecting a series of steered ultrasound scan lines 44 by using a two-dimensional array or a linear array at different positions. An ultrasound scan line includes both lines of data that have been actually collected by the transducer as well as the synthetic and analytic lines of data generated as a function of those collected ultrasound lines.

Each ultrasound line 44 is an edge 52 of the wire frame model 46. The ultrasound data samples 48 are on each ultrasound line 44. In addition, edges 52, such as AB, connecting the data samples 48 from adjacent lines 44 at the furthest distance from the transducer 12 is contained in the wire frame model 46. Also contained in the wire frame model 46 are edges 52, such as DC, connecting the data samples 48 from the adjacent lines 44 at the shortest distance from the transducer 12. As shown in FIG. 9, the elevation, θ, and the azimuth, Φ, dimensions correspond to different positioning of the origin of each ultrasound line 44. The data along each scan line 44 is provided on the range dimension. As shown in FIG. 9, the origins of the ultrasound lines are placed at locations generated by sampling the spaces, (θ, Φ), (θ, sin Φ), (sin θ, Φ) or (sin θ, sin Φ) in uniform steps. Other uniform or non-uniform sampling schemes, such as including but not limited to sampling in a hexagonal grid, may also be used.

FIG. 10 shows a simplified form of FIG. 9 with the wire frame model 46 for a three-dimensional volume acquired by using only 9 ultrasound lines 44: AP, BQ, CR, HW, KX, DS, GV, FU and ET, shown in broken lines. In practice, there are many more ultrasound lines 44 in the data set. The transducer surface 12 is at or close to the surface ABCDEFGHK. The 3D data set ends at the surface PQRSTUVWX, corresponding to the maximum range. The wire frame model, in this case contains the nodes: A, B, C, D, E, F, G, H, K, P, Q, R, S, T, U, V, W, and X. The wire frame model 46 also contains the edges 52, AP, BQ, CR, HW, KX, DS, GV, FU, ET, AB, BC, HK, KD, GF, FE, AH, HG, BK, KF, CD, DE, PQ, QR, WX, XS, VU, UT, PW, WV, QX, XU, RS and ST. The wire frame model 46 also contains the sides 42: ABQP, BCRQ, HKXW, KDSX, GFUV, FETU, AHWP, HGVW, BKXQ, KFUX, CDSR, DETS, PWXQ, QXRS, WVUX, XUTS, AHKB, BKDC, HGFK and KFED. In this embodiment, none of the "internal" sides 42 or edges 52 are excluded from the wire frame model, but one or more sides or edges may be excluded.

The second embodiment of the wire frame model 46 shown in FIG. 10 may be decomposed into a collection of wire frame models 46 belonging to the first embodiment shown in FIG. 3. For example, the wire frame model 46 shown in FIG. 10 can be decomposed into two sub-wire frame models containing the nodes AHGFKBPWVUXQ and BKFEDCQXUTSR. In this case, the internal side, HKXW is excluded from the sub-wire frame model, AHGFKBPWVUXQ and the internal side, KDSX from the sub-wire frame model, BKFEDCQXUTSR. Therefore, the second embodiment of the wire frame model 46 can be reduced to the first embodiment of the wire frame model 46. Therefore, if this approach is taken, all the methods and steps outlined in the present application for the first embodiment of the wire frame model include those for the second embodiment of the wire frame model. Alternatively, the wire frame model 46 of the embodiments of FIGS. 9 and 10 are processed without decomposition.

If there are K ultrasound lines 44 in the three-dimensional data set, the wire frame model 46 also contains K edges 52, such as .DA, CD, FE . . . corresponding to these ultrasound lines 44. In practice, the number of edges 52, such as DA, CD, FE, . . . , in the wire frame model can be reduced for a given K (e.g., reducing to K/4), resulting in increased processing speed, at the expense of image quality of the final volume rendered image.

III. Texture Coordinates

In APIs such as OpenGL and DirectX, three floating point numbers, s, t, and r, known as "texture coordinates" and each in the range of [0.0, 1.0], are used to describe a particular ultrasound data sample 48 out of the possible N such samples, a particular one-dimensional data array out of the possible M such arrays and a particular two-dimensional data array out of the possible L such arrays, respectively. For example, if L=4, M=8 and N=4, the first two-dimensional data array in the three-dimensional data set corresponds to r=0.0, the second to r=0.33, the third to r=0.67 and the last to r=1.0. Similarly, the sixth one-dimensional data array M in a given two-dimensional data array L corresponds to t=0.83 and the third ultrasound data sample N in a given one-dimensional data array M corresponds to s=0.67. Note that r=0.5 corresponds to a two-dimensional data array L between the second and third two-dimensional data arrays L. This two-dimensional data array is not associated with a particular scan by the transducer 12. The GPU synthesizes this two-dimensional data array using interpolation of neighboring ultrasound data samples.

Figure 4:
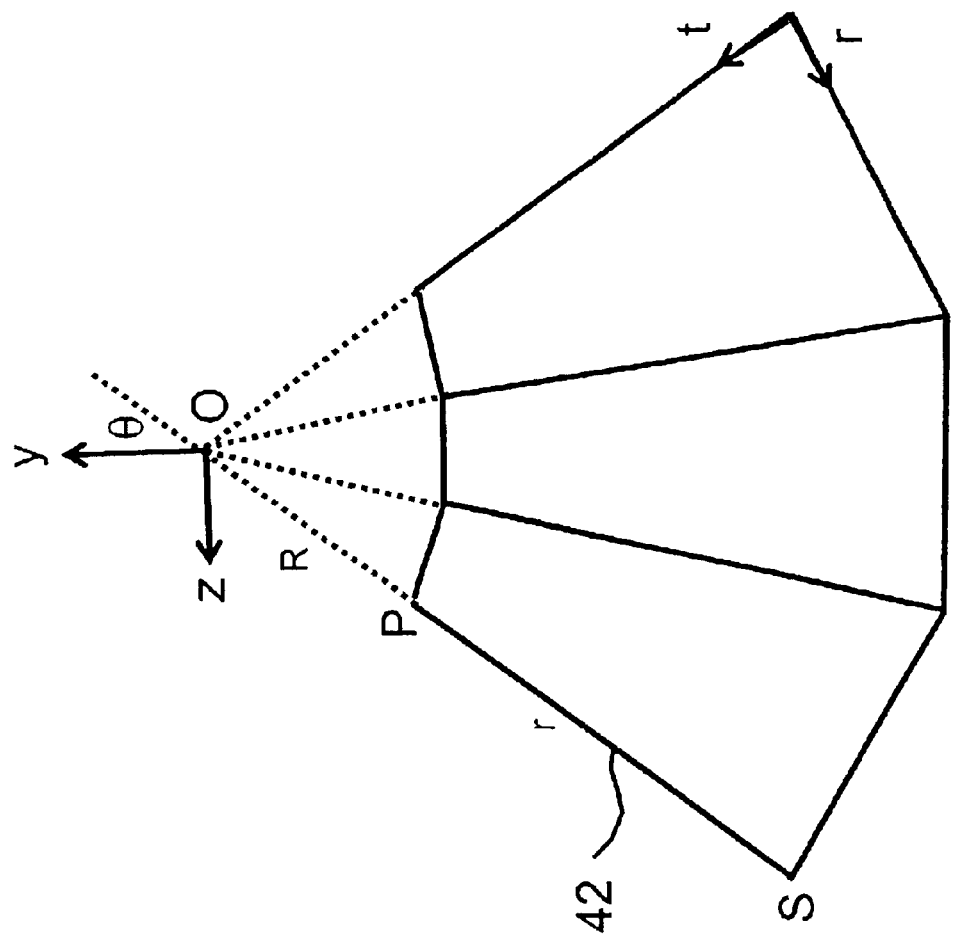
FIG. 4 is a graphical representation of the wire frame model shown in FIG. 3 when viewed along the x-axis.

For the first embodiment of the wire frame model 46 shown in FIG. 3, the Cartesian coordinate system, (x, y, z) and the texture coordinate system (s, t, r) are shown. The texture coordinates, (s, t, r), relate to the Cartesian coordinates, (x, y, z) as a function of various parameters as shown in FIG. 4. FIG. 4 is a view of FIG. 3 viewed along the x-axis. The parameters, R, r, θ and xFov define the wire frame model 46 and the texture coordinates. The parameter R is the distance from the origin, O, to the top edge of a two-dimensional ultrasound data frame. The parameter, r, is the height of the two-dimensional ultrasound data frame (line QR in FIG. 3). The parameter, θ, is the angle made by the first and the last scan planes with the y-axis. The angle between the first and the last scan planes is 2θ. The parameter xFov is the width of a 2D ultrasound data frame (line PQ in FIG. 3).

The texture coordinates, (s, t, r), for any given (x, y, z) position is determined from the following equations.

$$s = \frac{x + \frac{xFov}{2}}{xFov} \qquad \text{Equation 1}$$

$$t = \frac{[R+r] - \sqrt{y^2 + z^2}}{r} \qquad \text{Equation 2}$$

$$r = 1 - \frac{\arctan\left(\frac{z}{y}\right) + \theta}{2\theta} \qquad \text{Equation 3}$$

The above equations specify which ultrasound data sample 48 or samples in the three-dimensional ultrasound data set correspond to a given point, (x, y, z), in the Cartesian coordinate system.

IV. Alpha Blending

The display 24 in FIG. 1 displays what is in the "frame buffer," i.e., a segment of the memory 22. Every element in the display corresponds to a fixed number of bytes of memory. Typically, an element in the display corresponds to 4 bytes of memory, called a pixel. In this case, one byte is allocated for the colors red, green and blue, respectively. The remaining byte is allocated for a weight known as the "alpha weight." Initially, the pixels are cleared or set to a fixed value. When ultrasound data is rendered to the frame buffer, the content of a pixel is updated. If alpha blending is disabled, the content of a pixel after rendering contains the data from the present ultrasound data. If the alpha blending is enabled, the content of the pixel after rendering contains a weighted sum of the data from the present ultrasound data and the previous content of the pixel, prior to rendering. Using an API such as OpenGL or DirectX, the weights may be changed.

V. Volume Rendering Using Texture Mapping

When using an API, such as OpenGL or DirectX for volume rendering a three-dimensional data set, the data set first is loaded into the GPU memory. A series of parallel planes through the data set, all orthogonal to the viewing direction, is rendered from back to front, while the data in each cut-plane is blended with what is already rendered to the screen. The term "back" refers to a location furthest away from the observer while the term "front" refers to a location nearest to the observer. Data from the three-dimensional data set that is in the cut-plane is painted or used for rendering. The number of parallel cut-planes used determines the quality of the volume rendering. The higher the number of cut-planes, the better the quality, the higher the chances of saturation of the frame buffer and the slower the rendering speed. For a three-dimensional data set of the size L×M×N data samples, the number of cut-planes may be the square root of (L×L+M×M+N×N), but fewer or greater cut-planes may be used. If there is a priori knowledge that the ultrasound data corresponding to a given cut-plane or a part thereof is predominantly black (e.g., zero) or uniform, that particular cut-plane or a part thereof need not be rendered, thus increasing the rendering speed.

To render a cut-plane with the corresponding ultrasound data, the intersection of the cut-plane with the physical extent of the three-dimensional data set, specified by the wire frame model 46, is first computed. Then, the intersection is broken down into a series of quadrilaterals or triangles. The vertices of these quadrilaterals or triangles are defined in a global reference coordinate system, such as (x, y, z) defined in FIG. 3. In addition, the texture coordinates (s, t, r) for each vertex, are also specified. The vertices and the texture coordinates of these quadrilaterals or triangles are then passed onto the GPU to render the intersection, and hence the cut-plane.

The following OpenGL code segment is used to load a three-dimensional volume of ultrasound data, image, of width, iWidth, height, iHeight and depth, iDepth, into the GPU.:

```
glTexImage3DEXT(GL_TEXTURE_3D, 0, GL_RGBA, iWidth,
   iHeight, iDepth, 0, GL_RGBA, GL_UNSIGNED_BYTE,
   image);
```

The following code segment is used to define the weights for alpha blending and to enable alpha blending:

```
glBlendFunc(GL_ONE, GL_SRC_ALPHA);
glEnable(GL_BLEND);
```

The following code segment are used to render a cut-plane defined by the vertices of the intersection contained in the array, verts and the texture coordinates contained in the array, texCs:

```
float *vptr = verts;
float *tptr = texCs;
glBegin(GL_TRIANGLE_STRIP);
for (ii = 0; ii < nVertices; ii++) {
    glTexCoord3f(*(tptr++), *(tptr++), *(tptr++));
    glVertiex3f(*(vptr++), *(vptr++), *(vptr++),);
}
glEnd( );
```

The pair of commands glTexCoord3f and glVertex3f taken together associates an ultrasound data sample defined by the texture coordinates with a vertex of the intersection in the global reference coordinate system, (x, y, z). The above code segment performs this association for all the vertices of the intersection. This enables the GPU to compute the ultrasound data samples everywhere inside the intersection using interpolation of the ultrasound data. Although the OpenGL directive glBegin(GL_TRIANGLE_STRIP) is used to encapsulate the texture coordinates and the Cartesian coordinates of a vertex, other OpenGL directives, such as glBegin(GL_TRIANGLE_FAN), glBegin(GL_QUADS), glBegin(GL_QUAD_STRIP), glBegin(GL_POLYGON), glBegin(GL_TRIANGLES) or their equivalents in DirectX can also be used. Although the above code segments are written using OpenGL API, similar code segments also exist in other APIs such as DirectX. Custom coding may also be used.

VI. Example Embodiments

Figure 2:
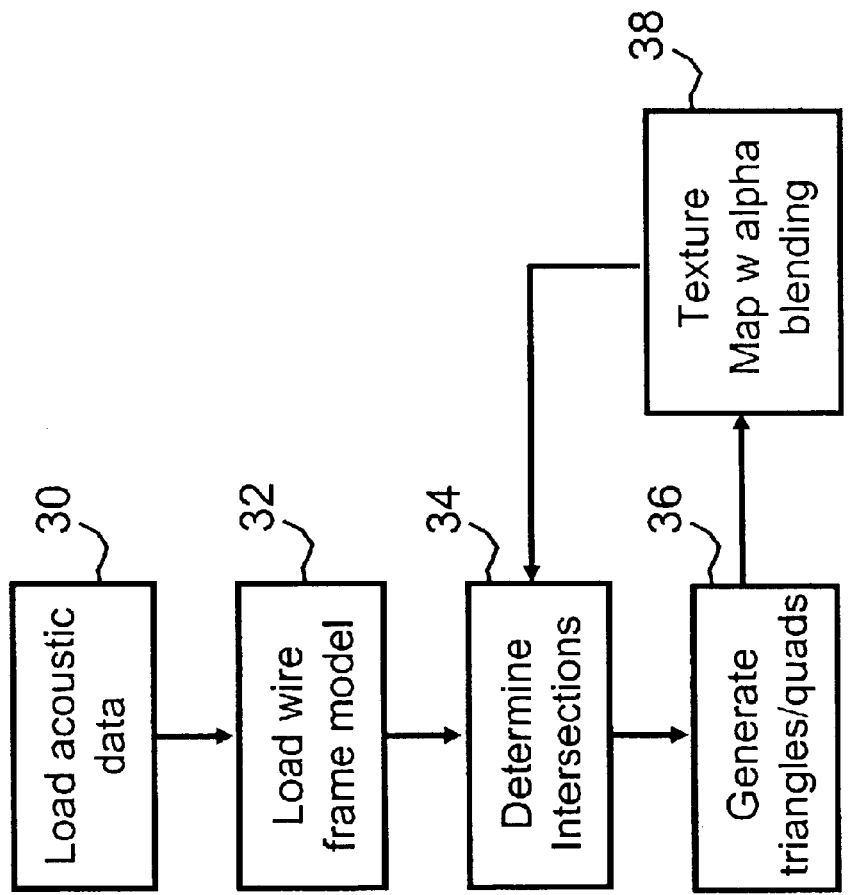
FIG. 2 is a flowchart diagram of on embodiment of a method of volume rendering ultrasound data for three-dimensional imaging.

FIG. 2 shows a flowchart of one embodiment a method for volume rendering ultrasound data for three-dimensional imaging. In act 30, ultrasound data formatted at least in part in an acoustic grid is loaded into the GPU 20. The ultrasound data is loaded into the video RAM or memory 22 of the GPU 20 as texture data. The acoustic data preferably is in a form generated by the ultrasound system after detection and log-compression, although post log-compression data may also be used. The ultrasound data comprises data in a substantially entire polar coordinate format (see FIGS. 9 and FIG. 10), such as data free of Cartesian coordinate formatting. Alternatively, the ultrasound data includes partially scan-converted images of ultrasound data spaced in an acoustic grid within the volume (see FIG. 3). The ultrasound data in the acoustic grid is loaded into the memory 22 as a function of the spatial orientation of the image planes or scan lines.

The speed of loading the acoustic data as textures into the memory 22 can be increased by using compressed texture data formats. Texture compression is performed using OpenGL texture compression schemes such as S3TC. Any of other now known or later developed compression schemes may also be used. In alternative embodiments, no compression is used.

To volume render with the GPU 20 from the ultrasound data in the texture memory, the wire frame model 46 of the spatial relationship of the data in the acoustic grid is generated in act 32. The wire frame model 46 is generated on the fly or in real time using the stored scan format parameters of the acoustic grid or using the parameters of the wire frame model 46. Alternatively, the wire frame model 46 is generated by loading a pre-computed and stored wire frame model data from the memory.

Figure 5:
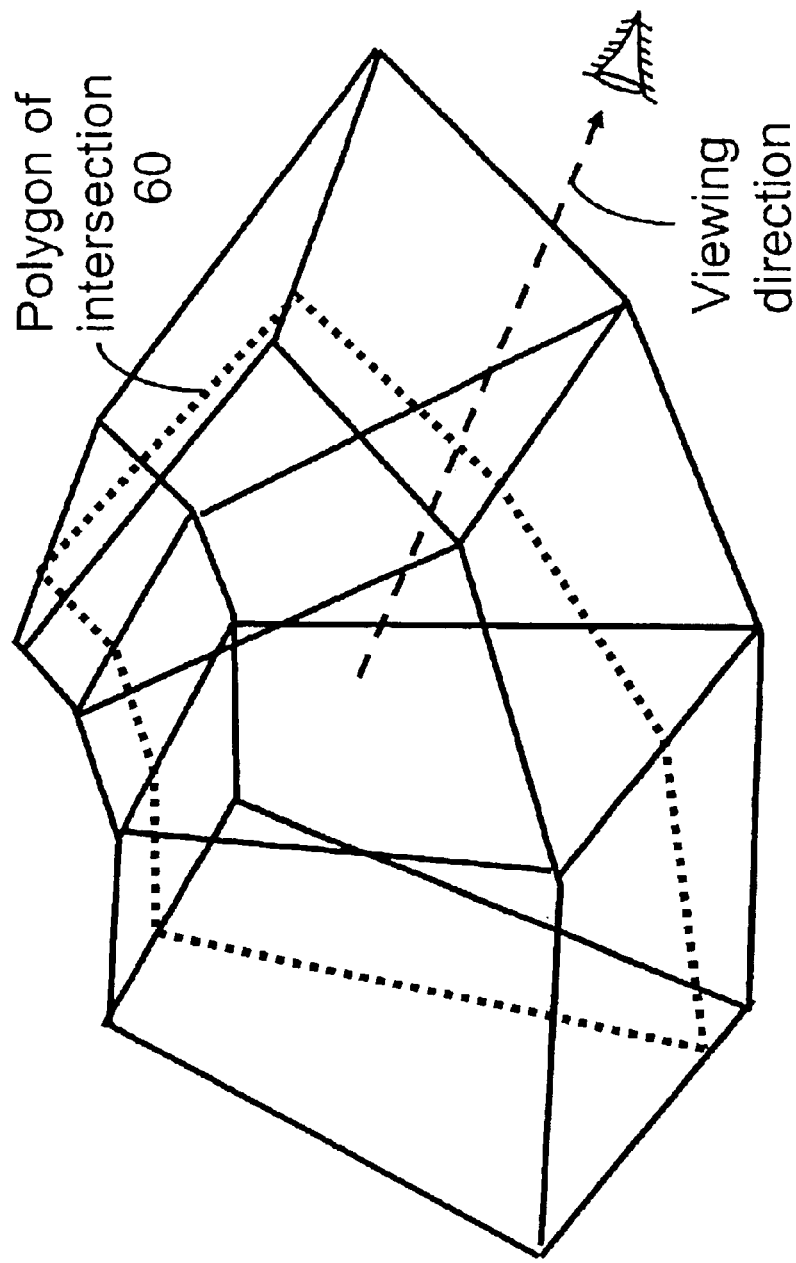
FIG. 5 is the wire frame model in the first embodiment with an arbitrary cut-plane orthogonal to the viewing direction, resulting in a polygon of intersection.

In act 34, the intersection between a cut-plane perpendicular to the viewing direction and the wire frame model 46 is determined, as shown in FIG. 5. Although the first embodiment of the wire frame model 46 is shown in FIG. 5, finding the intersection applies equally to the second embodiment of the wire frame model 46 as well. Since the wire frame model 46 is a collection of nodes (points), edges 52 (line segments) and sides 42 (planar polygons), the intersection is a collection of points and line segments. The points of the intersection are referred to as "vertices" and the line segments of the intersection are referred to as "line segments." In the more general case, the term cut-plane may be extended to include cut-surfaces perpendicular to the viewing direction. A spherical surface is an example of such a cut-surface. The act 34 is repeated using the processing loop shown in FIG. 2 for a plurality of parallel cut-planes perpendicular to the viewing direction, starting from the cut-plane furthest away from the viewer and ending at the cut-plane closest to the viewer. The viewing direction is arbitrary, selected by the user or selected by the GPU. The intersection planes are equally spaced or unequally spaced. Using more intersection planes may allow for greater resolution or information content of the volume rendering, but slower processing speeds.

A given plane intersects the wire frame model 46 at a plurality of edges 52 of the wire frame model. The point of intersection, P, is determined for each of the edge 52. For example, where a line segment extends from two points $P_0$ and $P_1$, the point of intersection P along the line $P_0\, P_1$ is given by:

$$P = P_0 \lambda + (1-\lambda) P_1 \quad \text{Equation 4}$$

where $\lambda$ is a value between 0.0 and 1.0 representing the normalized distance along the line segment 52 between the two points. A plane is given by:

$$P \cdot \underline{n} = d \quad \text{Equation 5}$$

where $\underline{n}$ is a normal vector to the plane and d is the distance to the plane from the origin of the coordinate system. Combining equations 4 and 5 provides a solution for $\lambda$ given by:

$$P_o \cdot \underline{n} \lambda + (1-\lambda) P_1 \cdot \underline{n} = d \quad \text{Equation 6}$$

$$\lambda \left[ P_o \cdot \underline{n} - P_1 \cdot \underline{n} \right] = d - P_1 \cdot \underline{n}$$

$$\lambda = \frac{d - P_1 \cdot \underline{n}}{(P_o - P_1) \cdot \underline{n}}$$

Figure 6:
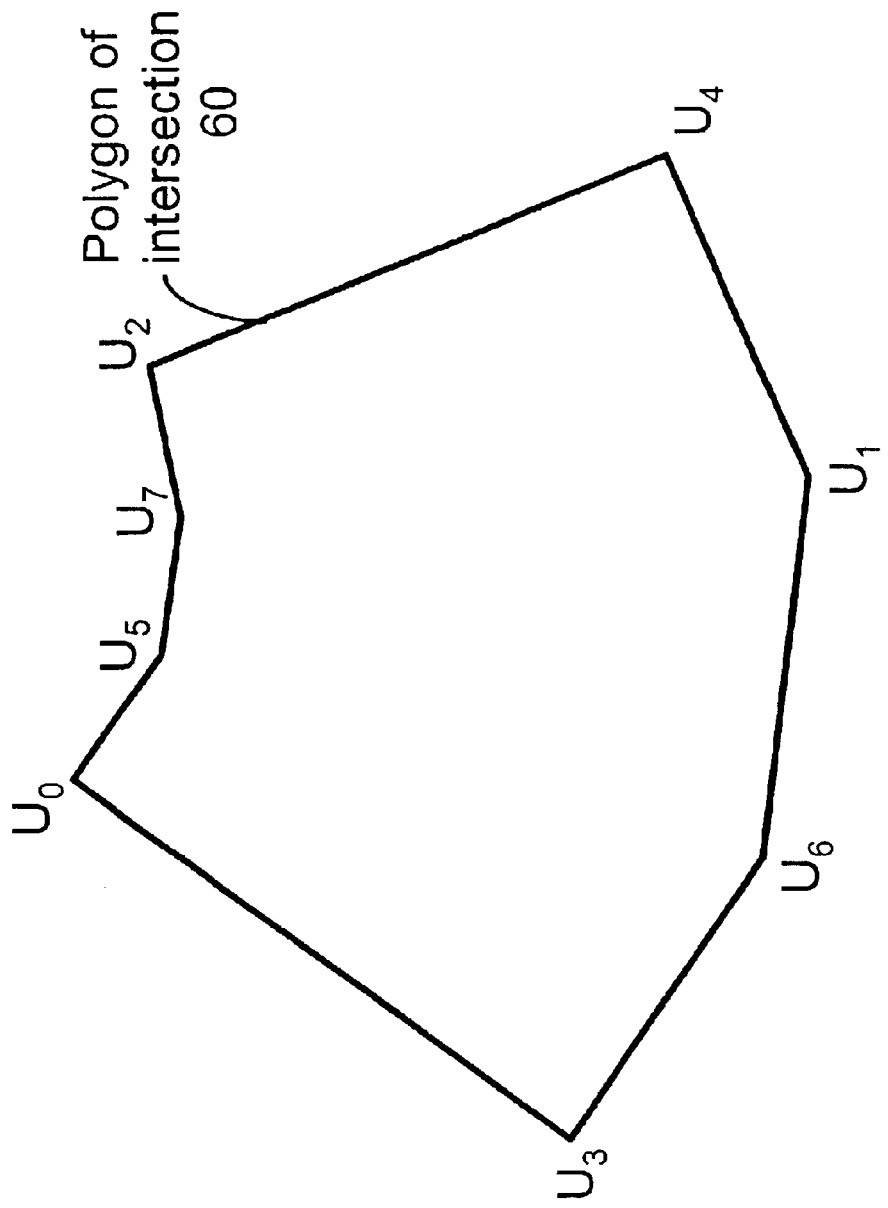
FIG. 6 is a graphical representation of the polygon of intersection from FIG. 5 and vertices generated by slicing the wire frame model in FIG. 3 using the cut-plane orthogonal to the viewing direction.

If the $0.0 <= \lambda <= 1.0$, then the point of intersection P is between $P_0$ and $P_1$. Otherwise, the plane does not intersect the particular edge 52 of the wire frame model. Where the plane of intersection is parallel to the edge, $\lambda$ would be positive or negative infinity and does not generate a point of intersection. For the first embodiment of the wire frame model shown in FIG. 3, the edges 52 are on the exterior surface of the wire frame model 46. In this case, the intersection represents, in general, a single polygon 60, such as the one shown in FIGS. 5 and 6. There may be two or more polygons of intersections, such as where the viewing direction is substantially parallel to the y-axis in FIG. 3 and the cut-plane intersects the wire frame model 46 at the very top, intersecting edges such as PD and QA. When there are two or more separate polygons 60 of intersection for one cut-plane, each polygon 60 is treated separately. The polygon 60 of intersection shown in FIG. 4 is planar, convex or concave, depending on the viewing direction. Each of the vertices, $U_i$, in the polygon 60 of FIG. 6 represents an edge 52 within the wire frame model 46. Each line segment between the vertices in FIG. 6 corresponds to a three-dimensional side 42 of the wire frame model 46.

Figure 11:
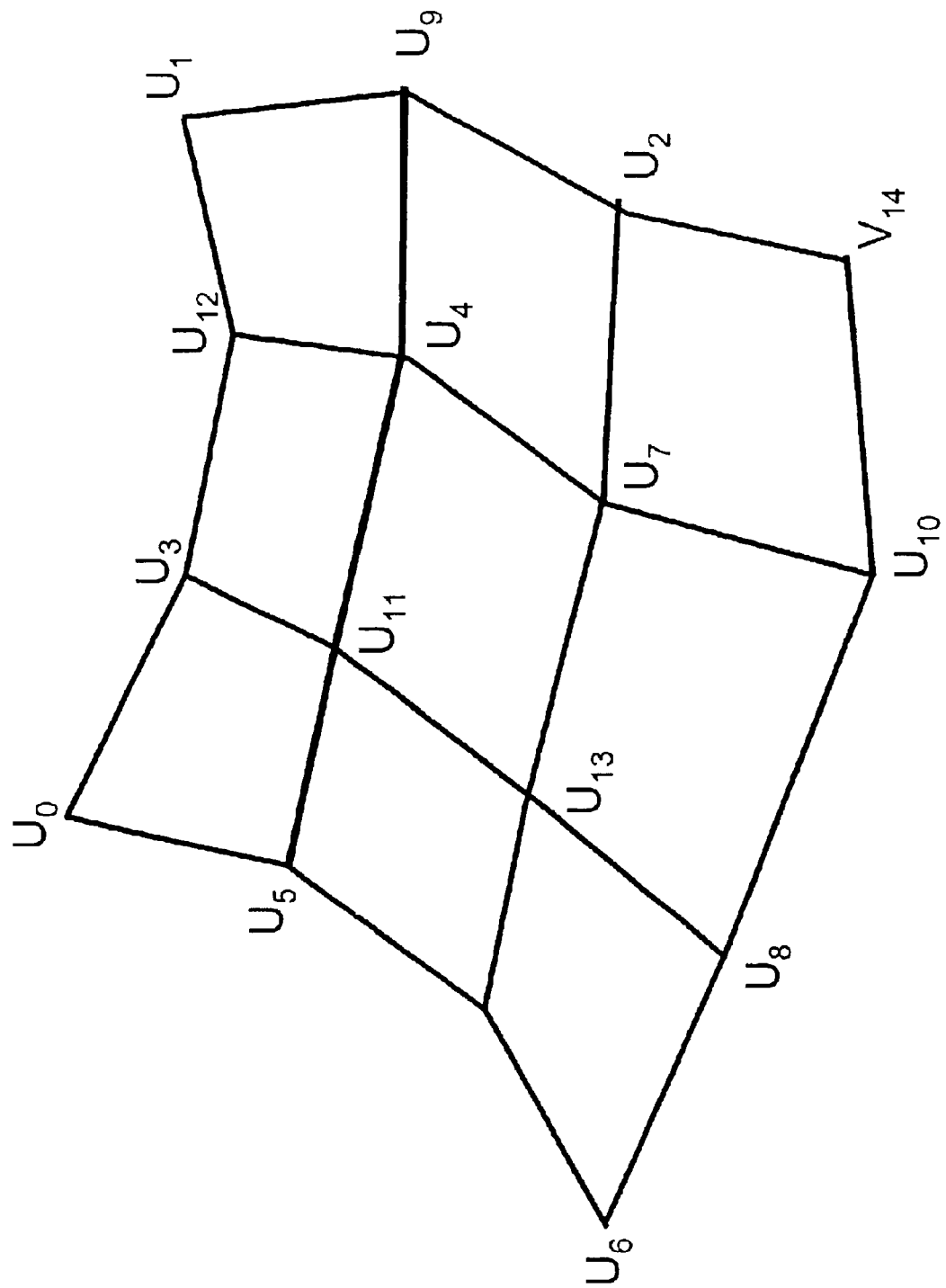
FIG. 11 is a graphical representation of the vertices and line segments in a plane of intersection generated by slicing the wire frame model shown in FIG. 9 with an arbitrary cut-plane.

The wire frame model 46 in the second embodiment shown in FIGS. 9 and 10 may be decomposed into a set of wire frame models from the first embodiment. One way to find the intersection for this second embodiment is to follow the acts outlined for the first embodiment above. Alternatively, the wire frame model 46 of this second embodiment is treated as a wire frame model distinct from the first embodiment. For the second embodiment of the wire frame model 46 shown in FIGS. 9 and 10, some edges 52, such as FE in FIG. 9 and KX in FIG. 10, are interior to the wire frame model 46. The intersection represents, in general, a fragment of a mesh bounded by a polygon, as shown in FIG. 11. There are several special cases where there may be several contiguous fragments of meshes, such as where the viewing direction is substantially parallel to the edge KX in FIG. 10 and the cut-plane is intersecting the wire frame model 46 at the very top, intersecting edges such as AH, BK, CD, HG, KF and DE. When there are more than one contiguous fragments in the intersection, each fragment is treated separately and independently.

In act 36, triangles or quadrilaterals (quads) are generated from the polygon 60 of intersection. The APIs, such as OpenGL or DirectX, expects a set of triangles or quads to render a cut-plane through the three-dimensional volume using texture mapping. In the following discussion, the intersections are assumed to be broken down into triangles since triangles are the most fundamental polygonal elements in OpenGL or DirectX. Even when quads are specified, the API breaks them down to triangles. Quads, triangle or other divisions may be used.

To generate the triangles for the polygon 60 of FIG. 6, the vertices $U_i$ of the polygon 60 are converted into an ordered set to be treated as a series of triangles. Given a set of vertices $U_i$, the ordered set of vertices $V_i$ is generated. One vertex, such as $U_0$ shown in FIG. 6, is selected as the starting vertex. Then, a connected component search along the sides 42 of the wire frame model 46 of FIG. 3 is performed to form an intermediate ordering of vertices. Each edge 52 of the wire frame model 46 in FIG. 3 that intersects with the cut-plane produces at most one vertex belonging to the polygon 60. Each edge 52 in the wire frame model 46 is also associated with two different sides 42 in the wire frame model 46. Each vertex, $U_i$, of the polygon 60 is thus associated with two sides 42 of the wire frame model 46. Each side 42 has four edges 52 and four nodes. If the plane is intersecting a side, there are exactly two edges 52 of the side 42 intersecting the plane as well. In the corner case where a plane is intersecting the side 42 at a node, the above statement is still true since there are two edges intersecting the plane at the node shared by the two edges 52, with the result that the intersecting vertices are identical.

Figure 7:
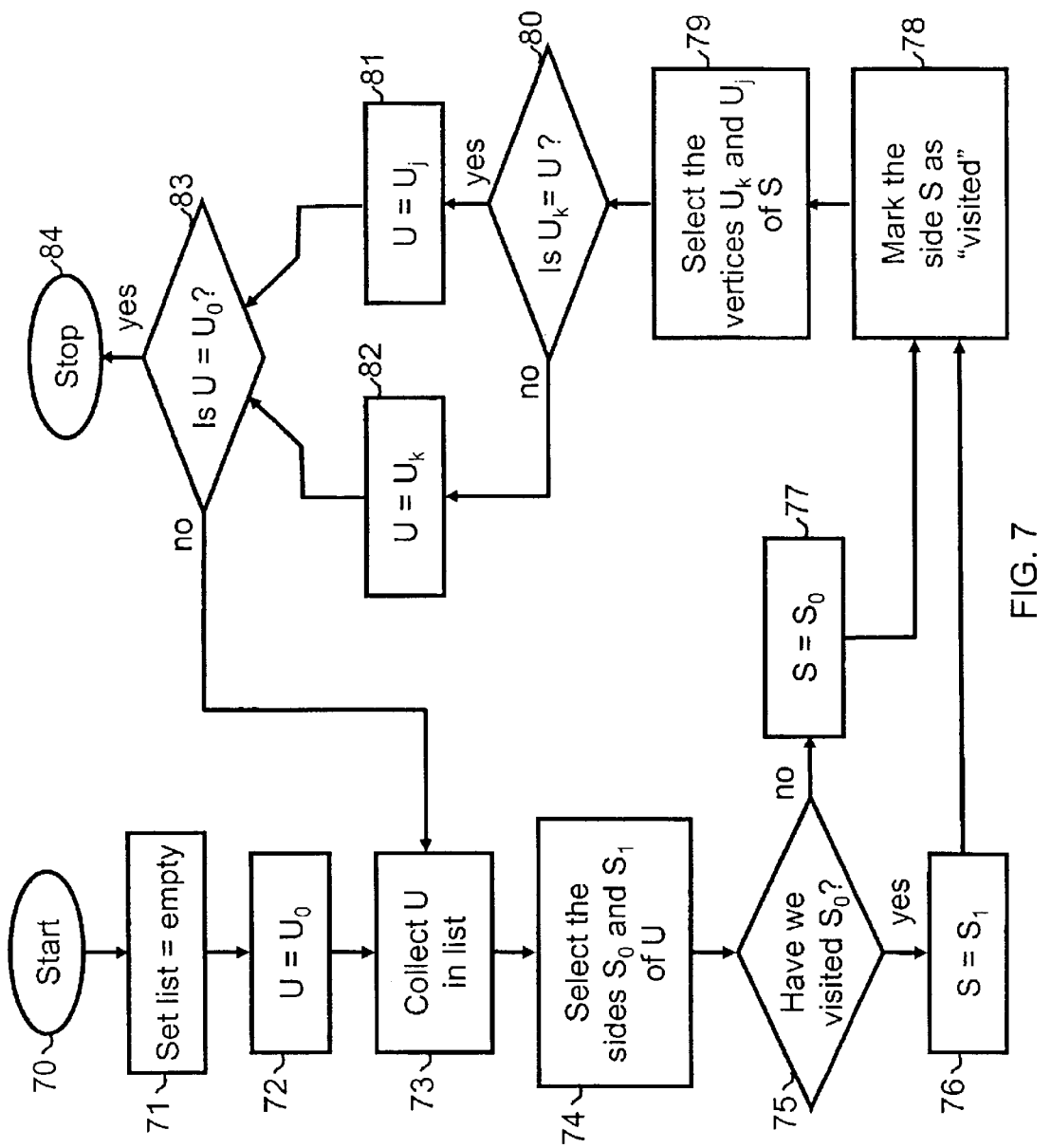
FIG. 7 is a flowchart diagram showing the steps of ordering the vertices to generate triangles or quadrilaterals in one embodiment.

The algorithm for ordering the set of vertices, $U_0$, into an intermediate ordering is shown in FIG. 7. In act 71, the list containing the resulting ordered list of vertices is initialized to an empty list. In act 72, the working vertex, U, is set to the initial vertex, $U_0$. In act 73, U is added to the list. In act 74, the two sides associated with U are selected. In acts 75–77, the first side out of the two sides that has not already been visited is selected and labeled as S. In act 78, S is tagged as "visited". In act 79, the two vertices associated with S are selected. In acts 80–82 82, the vertex belonging to S that is different from U is selected and the new vertex is labeled as U. In act 83, U is checked against $U_0$ to see if the process has returned to the starting vertex. If at the starting vertex, the process stops and outputs the list as the result. Otherwise, the process returns to act 73 and repeats.

Figure 8:
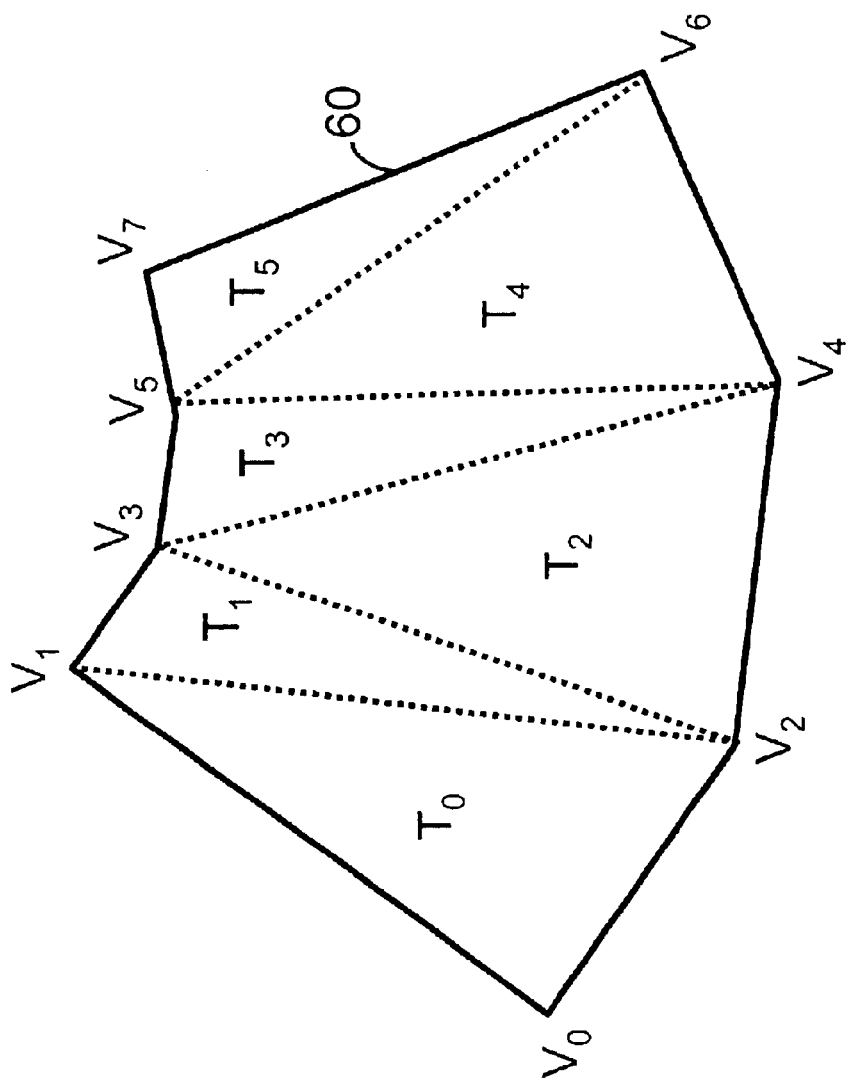
FIG. 8 is to the graphical representation of FIG. 6 with the vertices ordered to form triangles.

The sequence of vertices in the list output by the above process is the sequence of vertices of the polygon 60 going in clockwise or counter clockwise direction. Let $W_0, \ldots, W_{N-1}$ be the sequence of vertices in the above list. This sequence corresponds to the intermediate ordering. A new sequence is generated by re-ordering $W_i$ as follows:

$\{W_0, W_{N-1}, W_1, W_{N-2}, W_2, W_{N-4}, \ldots, W_{(N-2)/2}, W_{N/2}\}$
  if N is even
OR
$\{W_0, W_{N-1}, W_1, W_{N-2}, W_2, W_{N-4}, \ldots, W_{(N-3)/2}, W_{(N+1)/2}, W_{(N-1)/2}\}$ if N is odd This resulting sequence of vertices corresponds to the triangles of the intersection. FIG. 8 shows this sequence, renamed as $V_i$. As can be seen, if $V_i$, $V_{i+1}$, and $V_{i+3}$ are a sequence of consecutive vertices in this new list, they form a triangle. If there are N vertices in this new sequence, there will be N−2 triangles generated by the sequence $V_i$.

In alternative embodiments, the vertices are ordered using other processes, such as finding the center of gravity associated with a polygon of intersection, followed by ordering the vertices according to the angle made by the line joining the vertex to the center of gravity with a fixed direction, such as the horizontal. The intermediate ordering of the vertices is then accomplished by sorting the above angles in the increasing or decreasing order. Other algorithms for ordering the vertices may be used.

Any of various other triangulation schemes may also be used to triangulate the polygon of intersection 60, such as Delaunay triangulation, Dirichlet tessellation or other triangulation schemes.

In one embodiment, the determination of the polygon of intersection, the ordering of the vertices and the generation of the triangles or other planar shapes are performed by the GPU 20, such as using the GPU's 20 programmable vertex processor. OpenGL extensions or DirectX instructions may be used to program the vertex processor. Assembler, such as Cg by nVidia Corporation, may also be used to program the vertex processor. In alternative embodiments, another processor on a graphics acceleration card or separate from the graphics acceleration card determines one or more of the polygon of intersection, the ordering of the vertices and/or generation of triangles.

There are several ways to generate the triangles for the second embodiment shown in FIGS. 9 and 10 of the wire frame model 46 using the intersection. For example, the intersection is decomposed into a collection of intersections generated by intersecting the cut-plane with a collection of wire frame models of the first embodiment. In this case, the acts described above are used to generate triangles for each component intersection.

Figure 12:
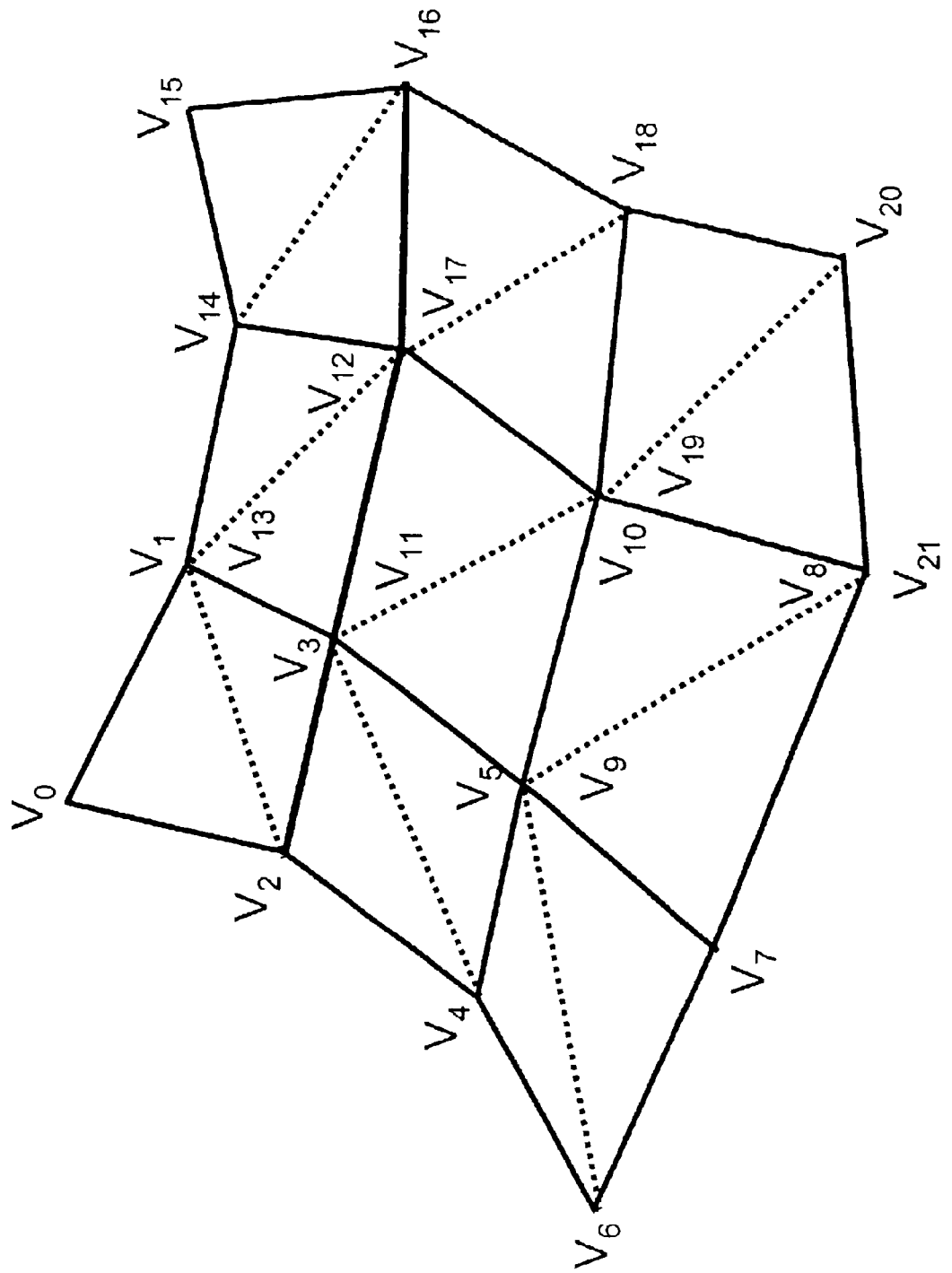
FIG. 12 is a graphical representation of the vertices in FIG. 11 after ordering to form triangles.

In another example, a connected component search starts from a vertex of the intersection associated with the exterior of the wire frame model 46 along the sides 42 of the wire frame model 46, similar to the connected component search performed for the wire frame model 46 of the first embodiment. FIG. 11 shows the intersection with its vertices, $U_i$. FIG. 12 shows the intersection after ordering the vertices to form triangles. In this example, there are three different sets of triangles, each set referred to as a "triangle strip." The first triangle strip is formed by the sequence of vertices: $V_0$, $V_1$, $V_2$, $V_3$, $V_4$, $V_5$, $V_6$ and $V_7$. The second triangle strip is formed by the sequence of vertices: $V_7$, $V_8$, $V_9$, $V_{10}$, $V_{11}$, $V_{12}$, $V_{13}$ and $V_{14}$. The third triangle strip is formed by the sequence of vertices: $V_{14}$, $V_{15}$, $V_{16}$, $V_{17}$, $V_{18}$, $V_{19}$, $V_{20}$ and $V_{21}$. Note that $V_3=V_{11}$, $V_5=V_9$, $V_{10}=V_{19}$, and $V_{12}=V_{17}$. More or fewer triangle strips may be used.

FIG 8. shows the vertices $V_i$ after ordering the vertices $U_i$ for the polygon 60 of intersection using the wire frame model of FIG. 3. After ordering, the sequence of vertices $V_0$, $V_1$ and $V_2$ corresponds to the vertices of the triangle $T_0$. The sequence of vertices $V_1$, $V_2$ and $V_3$ corresponds to the vertices of the triangle $T_1$ and so on. FIG. 12 shows the vertices after ordering for the polygon 60 of intersection using the wire frame model 46 of FIG. 8. When the sequence of vertices are sent to the GPU, along with their texture coordinates calculated as discussed above, encapsulated within the OpenGL directives glBegin(GL_TRIANGLE_STRIP) and glEnd( ), the GPU renders the intersection 60.

In act 38, the intersection corresponding to the cut-plane is rendered using the data samples from the three-dimensional ultrasound data using texture mapping. The GPU 20 performs the texture mapping with alpha blending. The mapping is a function of the intersection of the wire frame model 46 as identified by the vertices, $V_i$, and therefore, on the triangles, $T_i$. The intersections of the cut-planes are rendered from back to front with alpha blending enabled, resulting in a volume rendered image of the three-dimensional data set.

In alternative embodiments, a maximum or minimum projection scheme is used where previous pixel values are either replaced or remain unchanged based on a comparison with a current value. The feedback function shown in FIG. 2 represents repeating the determination of intersections, generation of triangles/quads and texture mapping with alpha blending for each of a plurality of cut-planes.

Real time or non-real time volume rendering from data at least in part in the acoustic grid is provided by the GPU 20 using texture mapping. The conversion to texture space effectively scan converts the ultrasound data. Where the ultrasound data is in a cylindrical coordinate system, such as shown in FIG. 3 and associated with the rotation of two-dimensional scan planes about an axis, only the outer boundaries of the wire frame model grid 46 are used to identify intersections with each plane perpendicular the viewing direction. The texture coordinates for ultrasound data interior to the volume is interpolated linearly by the GPU 20. Where the ultrasound data is entirely in a polar coordinate format, such as shown in FIGS. 9 and 10, the scan lines or beams of the wire frame model grid are considered. The resulting intersecting polygons corresponding to a planar mesh as shown in FIG. 11 are then used for texture mapping and volume rendering by the GPU 20. The texture mapping and volume rendering performed by the GPU 20 results effectively in scan conversion of data in an acoustic or non-Cartesian grid to a Cartesian grid for the two-dimensional representation. By avoiding scan converting the entire volume of ultrasound data or providing for no scan conversion prior to volume rendering with the GPU 20, the overall amount of processing for generating the two-dimensional representation may be reduced.

Other rendering processes or capabilities of the GPU 20 may be used with the volume rendering discussed above. For example, shading is implementing with the volume rendering. Any of various now known or later developed shading techniques may be used.

Volume rendering is used to describe the process of generating a two-dimensional image representing a volume where data from within the volume contributes to the representation, such as through using a plurality of cut planes and applying alpha blending, minimum, maximum or other functions to the data along a viewing direction. Volume rendering is a technique for displaying three-dimensional data as a two-dimensional image on a computer screen. By volume rendering, the image is associated with opacity or transparency of some data relative to others, as opposed to a mere painting of planes bounding the data volume or a subset thereof, with data. In alternative embodiments, painting of planes bounding the data volume or a subset thereof may also be used. In yet other alternative embodiments, surface rendering may be used rather than volume rendering.

In ultrasonic imaging, the speckle variance in ultrasound images is reduced by compounding. Ultrasound data or pixels of ultrasound images associated with different scans of a same scan plane are averaged to generate a compounded two-dimensional image. Volume rendering may be used as a way of averaging. Since a series of cut-planes are rendered and summed using weights, the speckle variance in the volume rendered image is smaller compared to the original data.

Typically, a graphics accelerator has frame buffers accommodating 8 bits per color gun (R, G, B or alpha), 16 bits per color gun or 32 bits per color gun. If the frame buffer has 8 bit color guns, the dynamic range of the input data may be reduced to less than 8 bits without any loss of volume rendering image quality since a large number of cut-planes are summed with weights. In some cases, the reduction in dynamic range may avoid saturation of the frame buffer. In this case, a beamformer operable to output data comprising a number of bits per sample less than 8 bits, i.e. for example, 4 bits, may be used to achieve faster data throughput.

While the invention has been described above by reference to various embodiments, it should be understood that many changes and modifications can be made without departing from the scope of the invention. For example, any of various now known or later developed volume rendering techniques, graphic processing units and acoustic data formats may be used. Some or none of the volume rendering processing discussed above for FIG. 2 may be performed by processors other than the GPU 20.

It is therefore intended that the foregoing detailed description be regarded as illustrative rather than limiting, and that it be understood that it is the following claims, including all equivalents, that are intended to define the scope and spirit of this invention.

What is claimed is:

1. A method for volume rendering ultrasound data for three dimensional imaging, the method comprising:
   (a) loading ultrasound data formatted at least in part in an acoustic grid into a graphics processing unit (GPU); and
   (b) volume rendering with the GPU from the ultrasound data.

2. The method of claim 1 wherein (b) comprises volume rendering at least twenty five volumes a second for images at least 512x512 pixels.

3. The method of claim 1 wherein (a) comprises loading into a video random access memory of a graphics accelerator and (b) comprises volume rendering with the graphics accelerator.

4. The method of claim 1 wherein (a) comprises texture mapping compressed ultrasound data.

5. The method of claim 1 wherein (a) comprises loading data entirely in a polar coordinate format.

6. The method of claim 1 wherein (a) comprises loading data from a plurality of scan converted frames of ultrasound data spaced in an acoustic grid.

7. The method of claim 1 wherein (b) comprises volume rendering from ultrasound data free of conversion to a Cartesian coordinate format.

8. The method of claim 1 wherein (b) comprises:
   (b1) determining an intersection of a plurality of surfaces through the acoustic grid and perpendicular to a viewing direction;
   (b2) generating polygons for each of the plurality of surfaces; and
   (b3) alpha blending the ultrasound data as texture data as a function of the polygons.

9. The method of claim 8 wherein (b3) comprises rendering the ultrasound data as texture data within each of the polygons.

10. The method of claim 8 wherein (b1) comprises determining spatial coordinates, and (b2) comprises texture mapping with an application programming interface based on the spatial coordinates.

11. The method of claim 1 wherein (b) comprises:
    (b1) identifying points of intersection between a surface and line segments of the acoustic grid;
    (b2) mapping the ultrasound data as texture data, the mapping being a function of the points of intersection.

12. The method of claim 1 wherein (a) comprises loading data from a plurality of scan converted frames of ultrasound data spaced in an acoustic grid, and (b) comprises:
    (b1) identifying vertices of intersection between the frames of ultrasound data and a surface;
    (b2) ordering the vertices;
    (b3) determining a plurality of polygons based on the ordered vertices;
    (b4) texture mapping the ultrasound data onto a plurality of polygons; and
    (b5) alpha blending the texture mapped ultrasound data.

13. An ultrasound system for volume rendering ultrasound data for three dimensional imaging, the system comprising:
    a memory operable to store ultrasound data formatted at least in part in an acoustic grid; and
    a graphics processing unit (GPU) connected with the memory, the GPU operable to volume render from the ultrasound data.

14. The system of claim 13 further comprising:
    a transducer; and
    a beamformer connected with the transducer, the beamformer operable to generate the ultrasound data in an acoustic grid.

15. The system of claim 13 further comprising a display, wherein the GPU is operable to generate images of at least 512x512 pixels at least twenty five times a second.

16. The system of claim 13 wherein the memory comprises a video random access memory.

17. The system of claim 13 wherein the GPU comprises a graphics accelerator.

18. The system of claim 13 wherein the GPU is operable to volume render from ultrasound data free of conversion to a Cartesian coordinate format.

19. The system of claim 13 wherein the GPU is operable to texture map the ultrasound data with an application programming interface as a function of an intersection of a plane with the acoustic grid.

* * * * *